United States Patent
Huang et al.

(10) Patent No.: US 7,992,428 B2
(45) Date of Patent: Aug. 9, 2011

(54) METHOD AND DEVICE FOR INGREDIENT ANALYSIS

(75) Inventors: Chia-Tsung Huang, Taipei County (TW); Wei-Chuang Lin, Taipei (TW); Hsiao-Ping Chang, Taipei County (TW)

(73) Assignee: General Standard Laboratory Co., Ltd., Sinjhuang, Taipei County (TW)

( * ) Notice: Subject to any disclaimer, the term of this patent is extended or adjusted under 35 U.S.C. 154(b) by 474 days.

(21) Appl. No.: 12/189,297

(22) Filed: Aug. 11, 2008

(65) Prior Publication Data
US 2009/0145204 A1 Jun. 11, 2009

(30) Foreign Application Priority Data
Dec. 7, 2007 (TW) .............................. 96146801 A

(51) Int. Cl.
*G01N 13/00* (2006.01)
(52) U.S. Cl. ...................... 73/61.55; 73/61.48; 73/61.52
(58) Field of Classification Search .................. 73/61.55, 73/61.52
See application file for complete search history.

(56) References Cited

U.S. PATENT DOCUMENTS

| 4,377,482 A * | 3/1983 | Rivier ............................. 210/635 |
| 5,970,804 A * | 10/1999 | Robbat, Jr. .................. 73/863.12 |
| 7,028,537 B2 * | 4/2006 | Karst et al. .................... 73/61.55 |
| 7,178,386 B1 * | 2/2007 | Gamble et al. ............... 73/61.57 |
| 2003/0115937 A1 * | 6/2003 | Ishii et al. ..................... 73/61.52 |
| 2008/0264801 A1 * | 10/2008 | West et al. ..................... 205/775 |
| 2009/0126466 A1 * | 5/2009 | Gilar et al. ................... 73/61.55 |

* cited by examiner

*Primary Examiner* — Hezron Williams
*Assistant Examiner* — Paul West
(74) *Attorney, Agent, or Firm* — Birch, Stewart, Kolasch & Birch, LLP

(57) ABSTRACT

A method for ingredient analysis includes the steps of: providing a database, which stores a plurality of standard ingredient data; analyzing a sample to obtain a plurality of inspection data via a high performance liquid chromatography (HPLC) method; and respectively comparing the inspection data with the corresponding standard ingredient data to analyze all ingredients contained in the sample simultaneously. The method may be applied to a device for ingredient analysis. Thus, by cooperating the database with the HPLC method, all ingredients contained in the sample can be analyzed via at least one analysis procedure so that the procedures for ingredient analysis are simpler and quicker and the accuracy of the analysis result can be enhanced.

13 Claims, 5 Drawing Sheets

METHOD AND DEVICE FOR INGREDIENT ANALYSIS

CROSS REFERENCE TO RELATED APPLICATIONS

This Non-provisional application claims priority under 35 U.S.C. §119(a) on Patent Application No(s). 096146801 filed in Taiwan, Republic of China on Dec. 7, 2007, the entire contents of which are hereby incorporated by reference.

BACKGROUND OF THE INVENTION

1. Field of Invention

The invention relates to an analysis method and device and, in particular, to a method and a device for ingredient analysis.

2. Related Art

The quality control and ingredient discriminating ability in medicine, cosmetic or food are very important researches. For example, the typical discriminating methods include an exterior description method, a microscopic discriminating method and a chemical class testing method. The chemical class testing methods include thin layer chromatography (TLC), beam splitter photometer, gas chromatography (GC), gas chromatography mass spectrum (GC-MS), liquid chromatography (LC) and liquid chromatography mass spectrum (LC-MS) methods.

Taking the commonly used TLC method as an example, the analyzing flow chart is shown in FIG. 1. First, in step S01, a developing tank is prepared. Next, in step S02, a silica gel TLC plate is provided to develop the menstruum, which may be a mixed solution composed of acetone, petroleum spirit, xylene and ethylmethylketone. In step S03, the sample solution with suitable concentration and the control compound solution with suitable concentration are prepared. The preparing method includes the steps of: taking a predetermined amount of solid (or powder) sample (or control compound); and dissolving the solid (or powder) sample (or control compound) in a solvent (e.g., acetone) to prepare the sample solution (or control compound solution) with the suitable concentration.

In step S04, a predetermined amount of sample solution and a predetermined amount of control compound solution, which are prepared in the step S03, are dropped at positions separated from each other by a predetermined distance at the bottom end of the TLC plate, and are then developed and dried. Next, in step S05, the TLC plate with the developed and dried sample solution and control compound solution is partially immersed in the menstruum until the menstruum is developed over the TLC plate to a certain distance. Finally, in step S06, the ratio of flow (Rf) of the appeared spots of the sample solution and the control compound solution on the TLC plate is inspected via a UV light source with the wavelength of 254 nanometers, thereby comparing the ingredients of the sample solution with those of the control compound solution.

However, when the ratio of flow (Rf) is being inspected via the TLC method, the human judging factors may seriously influence the final analysis result. In addition, the steps of the overall procedure are very complicated, time-consuming and labor-consuming, and the TLC method only can be restricted in analyzing some specific samples. In addition, in the qualitative analysis of the sample, two or more conditions have to be satisfied. Thus, the resolution and the sensitivity of the analysis result are poor. Nevertheless, compared with the TLC and the beam splitter photometer, the GC, GC-MS, LC and LC-MS methods need to spend a very long period of analyzing time to obtain the chromatography spectrum with well-separated effect in order to obtain the clearer and more definite analysis result. However, when the polarity range distribution corresponding to various ingredients in the sample is very wide, these ingredients stay in the separation columns for the very long time and thus influence the efficiency of the separation columns. Moreover, the analysis result may be interfered and the reproducibility of the analysis result is decreased.

Therefore, it is an important subject of the invention to provide a method and a device for ingredient analysis that can quickly and precisely analyze all ingredients contained in the sample.

SUMMARY OF THE INVENTION

In view of the foregoing, the invention is to provide a method and a device for ingredient analysis, wherein the analyzed inspection data of the sample can be compared with the standard ingredient data stored in a database so that the classes and/or contents of all ingredients contained in the sample can be quickly and precisely analyzed.

To achieve the above, the invention discloses a method for ingredient analysis. The method includes the steps of: providing a database, which stores a plurality of standard ingredient data; analyzing a sample to obtain a plurality of inspection data via a high performance liquid chromatography (HPLC) method; and respectively comparing the inspection data with the corresponding standard ingredient data to simultaneously analyze all ingredients contained in the sample. According to the method of the invention, the kinds and/or contents of the ingredients can be obtained in the step of analyzing the sample. Furthermore, after the step of analyzing all the ingredients contained in the sample, the method may further include the steps of adding at least one of standard ingredients, which corresponds to the ingredients contained in the sample, to the sample; and analyzing the sample with the added standard ingredient via the HPLC method. Therefore, the noise caused by impurities can be decreased during the analysis procedure.

In addition, the invention also discloses an ingredient analysis device for analyzing a sample. The ingredient analysis device includes a database, a sampling module and a comparing module. The comparing module is connected with the sampling module and the database. The database stores a plurality of standard ingredient data. The sampling module analyzes the sample via an HPLC method to obtain a plurality of inspection data. The comparing module respectively compares the inspection data with the corresponding standard ingredient data to simultaneously analyze all ingredients contained in the sample. According to the ingredient analysis device of the invention, the kinds and/or contents of the ingredients can be obtained. Moreover, the ingredient analysis device may further cooperate with a ultra-violet ray analyzing device and/or a mass spectrometer so as to enhance the accuracy of the analysis result.

As mentioned above, the method and the device for ingredient analysis according to the invention have the following features. By cooperating the database with the HPLC method, the inspection data is compared with the corresponding standard ingredient data after the sample encounters at least one analysis procedure. Thus, the classes and/or contents of all ingredients contained in the sample can be simultaneously analyzed. In addition, the accuracy of the analysis result can be enhanced by cooperating the analysis device, such as the HPLC apparatus, with the ultra-violet ray analyzing device, or cooperating the HPLC apparatus with the mass spectrometer. Furthermore, the corresponding standard ingredient can be added to the sample and another analysis procedure may be performed so that the noise generated due to the impurity can be decreased during the analysis procedure.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

The method and the device for ingredient analysis according to the invention can be applied to the process of analyzing the sample composed of a single component or multiple components, and can be applied to the ingredient analysis of the traditional Chinese medicine, western medicine, cosmetic or food. For example, the invention can be used to analyze whether the compound, the cosmetic or the food contains toxic ingredients, or whether the traditional Chinese medicine contains the ingredients of the western medicine.

Figure 1:
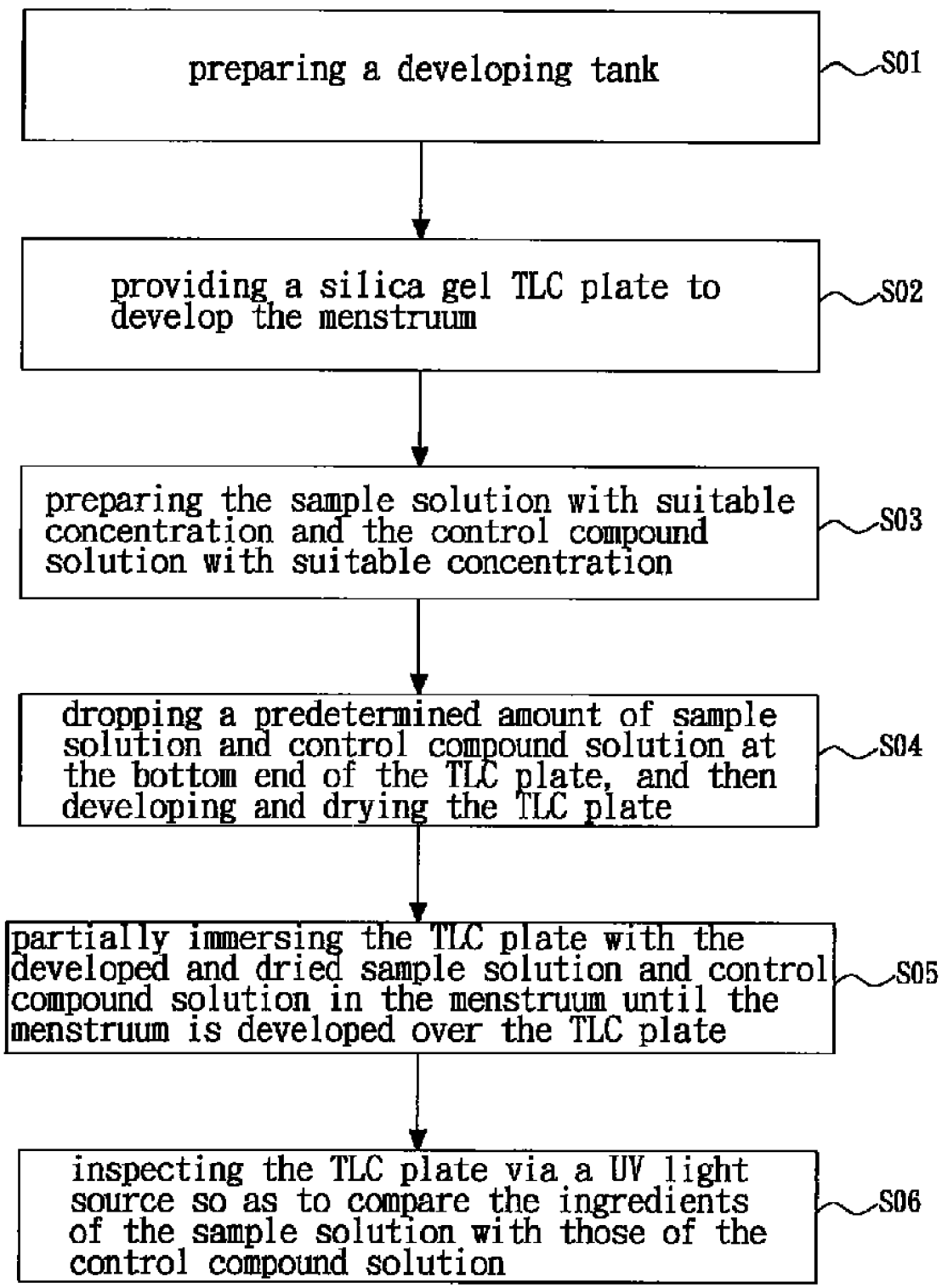
FIG. 1 is a flow chart showing a conventional TLC method.
Figure 2:
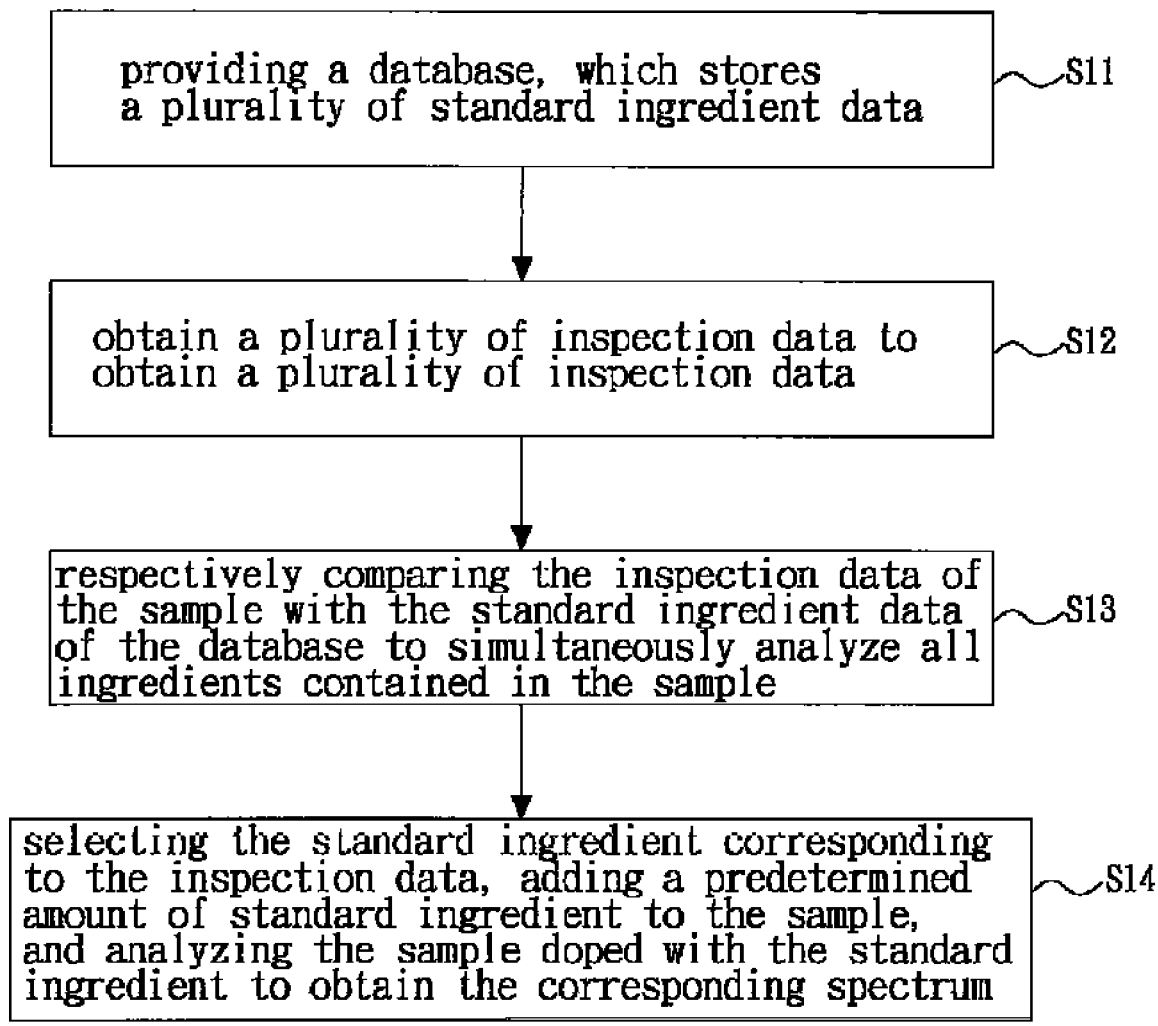
FIG. 2 is a flow chart showing a method for ingredient analysis according to a preferred embodiment of the invention.

Referring to FIG. 2, a method for ingredient analysis according to a preferred embodiment of the invention includes steps S11 to S14. First, a database is provided in the step S11. The database stores a plurality of standard ingredient data. Next, a sample is analyzed via an HPLC method in the step S12 to obtain a plurality of inspection data. Finally, the inspection data of the sample is respectively compared with the standard ingredient data of the database to simultaneously analyze all ingredients contained in the sample in the step S13.

Figure 3:
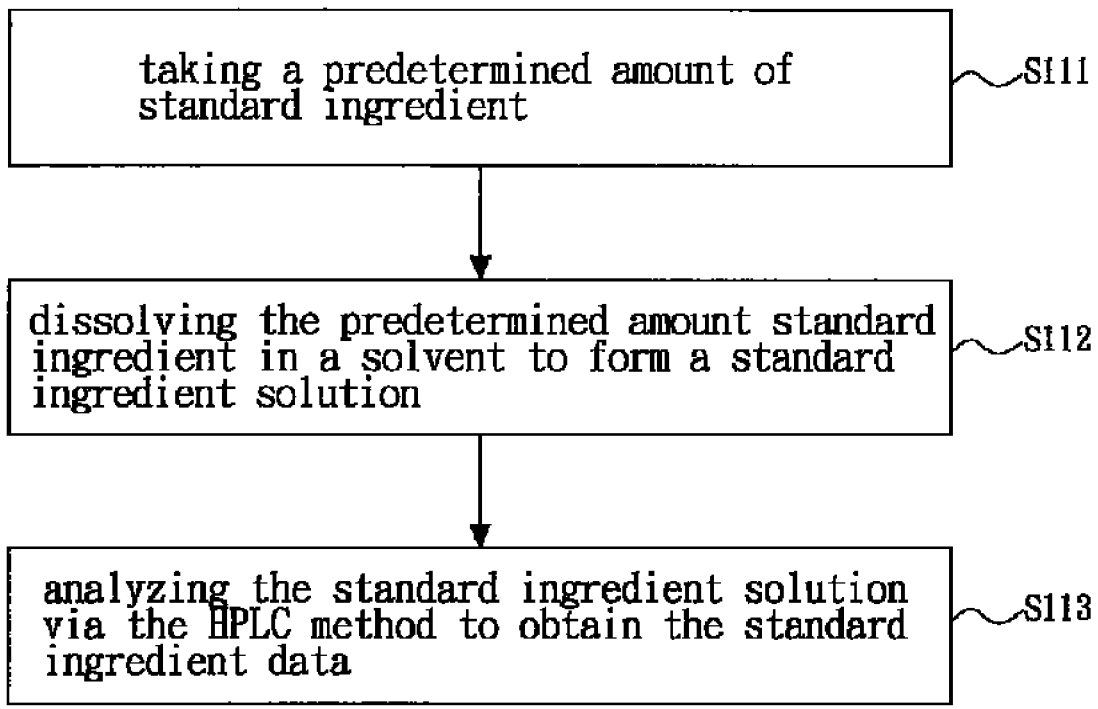
FIG. 3 is a flow chart showing steps of analyzing a standard ingredient via an HPLC method according to the invention.

In the step S11, the standard ingredient data may be obtained via any analyzing method. For example, when the standard ingredient data is obtained by analyzing the standard ingredient via the HPLC method, the analyzing process is shown in FIG. 3 and includes steps S111 to S113. First, the step S111 is to take a predetermined amount of standard ingredient. Next, in the step S112, the predetermined amount standard ingredient is dissolved in a solvent to form a standard ingredient solution. Finally, in the step S113, the standard ingredient solution is analyzed via the HPLC method to obtain the standard ingredient data. In addition, after the standard ingredient solution is prepared, the standard ingredient may be diluted to specific concentration with the same solvent or different solvents including, for example but not limited to, methanol.

In addition, in order to make all the ingredients corresponding to the sample analyzed by the HPLC method have higher resolution, the mobile phase injected into the HPLC apparatus may have different concentration variations with time so that the polarity difference between each ingredient of the sample and the mobile phase may become obvious via the concentration variation of the mobile phase. Thus, the retention time of the ingredients having the polarities similar to the mobile phase may be changed when the concentration of the mobile phase is changed with time. Thus, the ingredients having similar retention times may be separated out at different time instants. The mobile phase may be a single solvent or may be a mixture of many solvents including, for example but not limited to, acetonitrile and phosphoric acid. In addition, the pH value of the mobile phase may further be adjusted by other solvents, such as ammonia under a specific condition.

Figure 4:
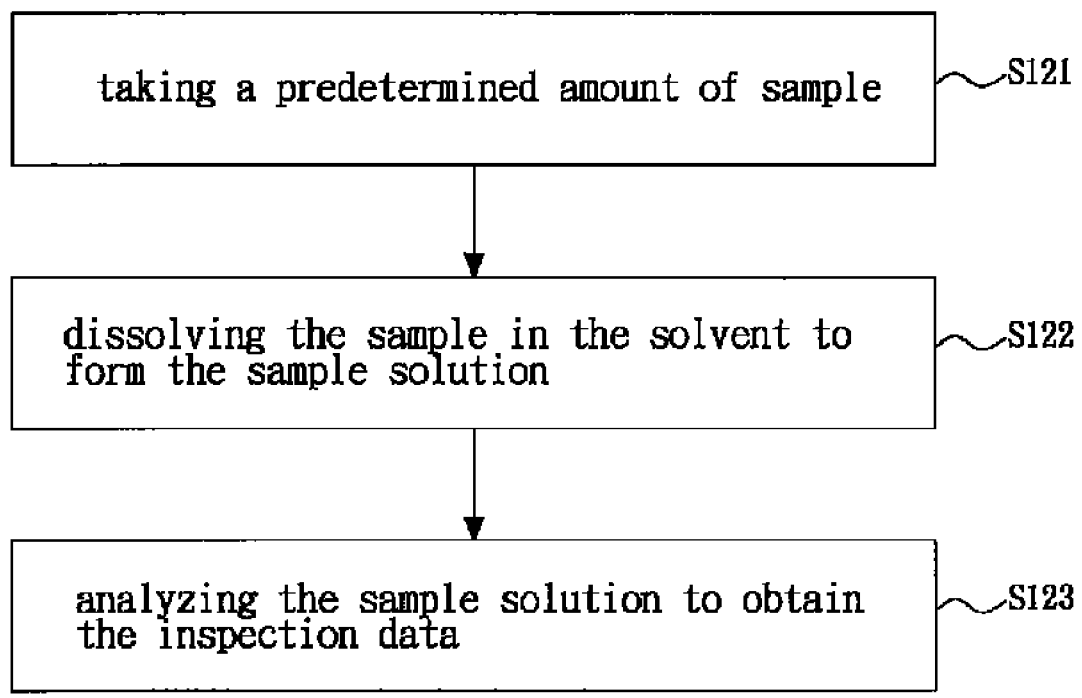
FIG. 4 is a flow chart showing steps of analyzing a sample via an HPLC method according to the invention.
Figure 5:
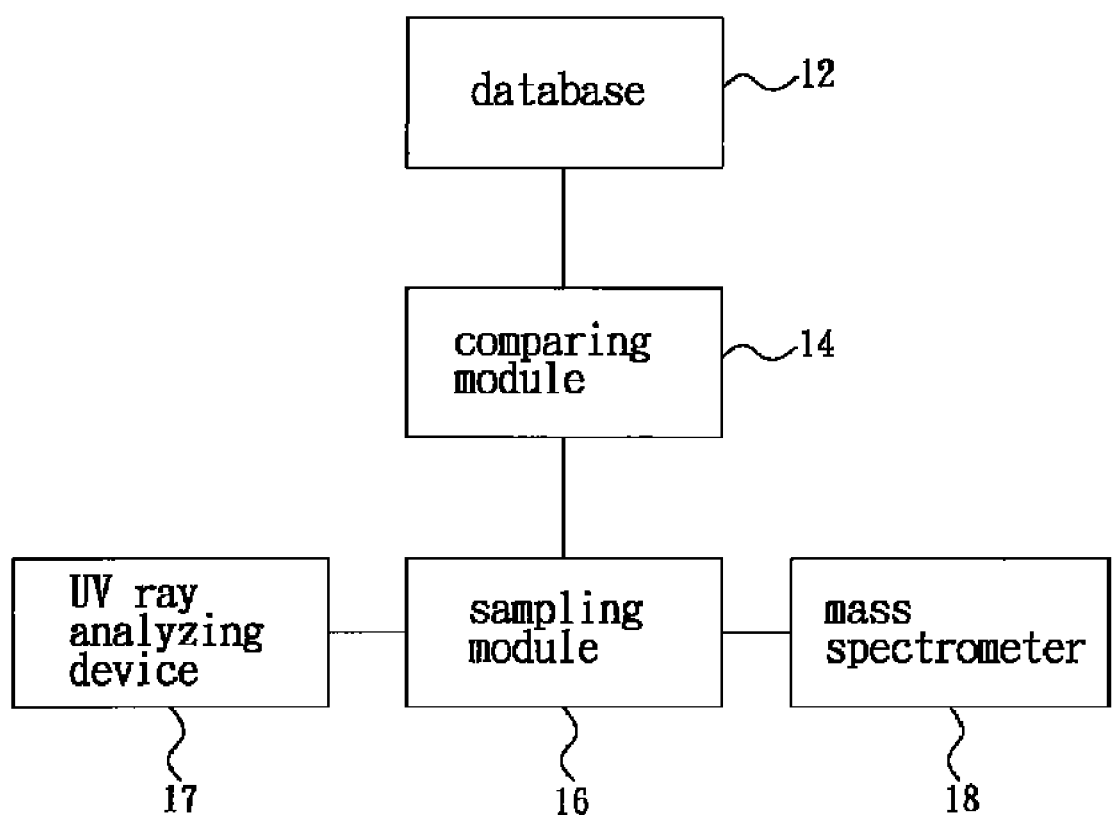
FIG. 5 is a block diagram showing an ingredient analysis device according to the preferred embodiment of the invention.

In the step S12, the sample may be formed into a sample solution before the sample is analyzed by the HPLC method. Referring to FIG. 4, this step S12 includes steps S121 to S123. First, the step S121 is to take a predetermined amount of sample. Second, the sample is dissolved in the solvent to form the sample solution, in the step S122. Finally, the sample solution is analyzed via the HPLC method in the step S123 to obtain the inspection data. Before the HPLC analyzing is performed, the sample solution may be firstly extracted and diluted according to the properties of different samples and the quality of the prepared sample solution. Thus, the concentration and the purity of the sample in the sample solution can be increased so as to enhance the accuracy of the analysis result. Of course, when the sample solution is being formed, the adopted solvent includes, for example but not limited to, the solvent of the sample solution.

Before the step S13 of FIG. 2 is performed, the data obtained via the HPLC method can be directly obtained to serve as the inspection data, and each ingredient separated by the HPLC apparatus may be further analyzed by a ultra-violet ray analyzing device or a mass spectrometer so that all ingredients can be analyzed. In addition, the data obtained by the ultra-violet ray analyzing device or the mass spectrometer may serve as the inspection data so that the accuracy of the analysis result can be enhanced.

In this embodiment, no matter which kind of analyzing data represents the inspection data, it is judged that the corresponding standard ingredient is contained in the sample when the spectrum similarity between the inspection data and the standard ingredient data is greater than 92%. When the spectrum similarity between the inspection data and the standard ingredient data is not greater than 92%, it is judged that the sample does not contain the corresponding standard ingredient. It is to be noted that the judgment standard is not restricted to 92% of this non-limitative embodiment.

After the step S13 of FIG. 2, the method may further include the step S14 in order to enhance the overall analysis accuracy. According to the comparing result of the inspection data and the standard ingredient data of the database, the standard ingredient corresponding to the inspection data is selected and a predetermined amount of standard ingredient is added to the sample. Then, a suitable analyzing method is performed to analyze the sample doped with the standard ingredient and the corresponding spectrum is obtained. As mentioned hereinabove, the analyzing method adopted herein may be the HPLC method, and all ingredients in the sample may further be analyzed by the ultra-violet ray analyzing device or the mass spectrometer after the HPLC analysis is performed.

When the spectrum similarity between the inspection data, which is obtained from the sample with the added standard ingredient, and the corresponding standard ingredient data is greater than 95% and no new waveform appears, it is judged that the sample indeed contains the corresponding standard ingredients. When the spectrum similarity between the inspection data, which is obtained from the sample with the added standard ingredient, and the corresponding standard ingredient data is not greater than 95% or a new waveform appears, it is judged that the sample does not completely contain the corresponding standard ingredients.

The solvent for dissolving and diluting the standard ingredient or the sample includes, for example but not limited to, methanol. The mobile phase includes, for example but not limited to, a mixed solution of acetonitrile and phosphoric acid, for example, and the pH value of the mixed solution of the acetonitrile and the phosphoric acid may be adjusted to about pH 3 by adding ammonia. In addition, when the extracting step is being performed, the sample solution with higher purity may be obtained by oscillating or centrifugal.

The method for ingredient analysis may be applied to the device for ingredient analysis. The ingredient analysis device according to the preferred embodiment of the invention includes a database 12, a sampling module 16 and a comparing module 14. The database 12 stores a plurality of standard ingredient data. The sampling module 16 analyzes the sample via the HPLC method to obtain a plurality of inspection data. The comparing module 14 is connected to the sampling module 16 and the database 12. When the sampling module 16 analyzes the sample via the HPLC method and thus obtains the plurality of inspection data, the sampling module 16 respectively compares the inspection data with the corresponding standard ingredient data of the database 12. According to the method for ingredient analysis, the classes and/or contents of all ingredients contained in the sample can be simultaneously analyzed.

The ingredient analysis device may further include a ultra-violet ray analyzing device 17 and a mass spectrometer 18. The ultra-violet ray analyzing device 17 is connected to the mass spectrometer 18 and the sampling module 16. By cooperating the HPLC apparatus with the ultra-violet ray analyzing device, or cooperating the HPLC apparatus with the mass spectrometer, the sample can be further analyzed so that the accuracy of the analysis result can be enhanced.

In summary, the method and the device for ingredient analysis according to the invention have the following features. By cooperating the database with the HPLC method, the inspection data is compared with the corresponding standard ingredient data after the sample encounters at least one analysis procedure. Thus, the classes and/or contents of all ingredients contained in the sample can be simultaneously analyzed. In addition, the accuracy of the analysis result can be enhanced by cooperating the analysis device, such as the HPLC apparatus, with the ultra-violet ray analyzing device, or cooperating the HPLC apparatus with the mass spectrometer. Furthermore, the corresponding standard ingredient can be added to the sample and another analysis procedure may be performed so that the noise generated due to the impurity can be decreased during the analysis procedure.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method for ingredient analysis, comprising the steps of:
   providing a database, wherein the database stores a plurality of standard ingredient data;
   analyzing a sample to obtain a plurality of inspection data via a high performance liquid chromatography (HPLC) method; and
   respectively comparing the inspection data with the corresponding standard ingredient data to simultaneously analyze all ingredients contained in the sample,
   wherein after the step of analyzing all the ingredients contained in the sample, the method further comprises the steps of:
   adding at least one of standard ingredients, which corresponds to the ingredients contained in the sample, to the sample; and
   analyzing the sample with the added standard ingredient via the HPLC method.

2. The method according to claim 1, wherein kinds and/or contents of the ingredients are obtained in the step of analyzing the sample.

3. The method according to claim 1, wherein the standard ingredient data is obtained by analyzing via the HPLC method.

4. The method according to claim 1, wherein the sample is formed into a sample solution in advance and then analyzed via the HPLC method.

5. The method according to claim 4, wherein the step of analyzing the same comprises the steps of:
   taking a predetermined amount of the sample;
   dissolving the sample in a solvent to form the sample solution; and
   analyzing the sample solution via the HPLC method to obtain the inspection data.

6. The method according to claim 5, wherein after the step of forming the sample solution, the method further comprises the step of:
   extracting the sample solution.

7. The method according to claim 6, wherein after the step of extracting the sample solution, the method further comprises the step of:
   diluting the extracted sample solution.

8. The method according to claim 1, wherein a mobile phase of the HPLC method is a mixed solution of acetonitrile and phosphoric acid.

9. The method according to claim 8, wherein the concentration of the mobile phase varies with time.

10. The method according to claim 1, wherein after the step of analyzing all the ingredients contained in the sample, the method further comprises the step of:
    analyzing the sample via a ultra-violet ray analyzing device.

11. The method according to claim 1, wherein after the step of analyzing all the ingredients contained in the sample, the method further comprises the step of:
    analyzing the sample via a mass spectrum method.

12. The method according to claim 1, wherein the inspection data obtained from the sample is compared with the corresponding standard ingredient data to analyze whether the sample contains the standard ingredient according to the conditions of:
    judging that the sample contains the standard ingredient when a spectrum similarity between the inspection data and the standard ingredient data is greater than 92%; and
    judging that the sample does not contain the standard ingredient when the spectrum similarity between the inspection data and the standard ingredient data is not greater than 92%.

13. The method according to claim 1, wherein the inspection data obtained from the sample having the added standard ingredient is compared with the corresponding standard ingredient data to analyze whether the sample contains the standard ingredient according to the conditions of:
    judging that the sample contains the standard ingredient when a spectrum similarity between the inspection data, which is obtained from the sample having the added standard ingredient, and the standard ingredient data is greater than 95% and no new peak appears; and judging that the sample does not contain the standard ingredient when the spectrum similarity between the inspection data, which is obtained from the sample having the added standard ingredient, and the standard ingredient data is not greater than 95% or a new peak appears.

* * * * *